(12) United States Patent
Czaja et al.

(10) Patent No.: US 8,461,074 B2
(45) Date of Patent: *Jun. 11, 2013

(54) COATED CATALYSTS COMPRISING A MULTIMETAL OXIDE COMPRISING MOLYBDENUM

(75) Inventors: Alexander Czaja, Dirmstein (DE); Martin Kraus, Westfield, NJ (US)

(73) Assignee: BASF SE, Ludwigshafen (DE)

( * ) Notice: Subject to any disclaimer, the term of this patent is extended or adjusted under 35 U.S.C. 154(b) by 214 days.

This patent is subject to a terminal disclaimer.

(21) Appl. No.: 12/937,210

(22) PCT Filed: Apr. 8, 2009

(86) PCT No.: PCT/EP2009/054238
§ 371 (c)(1),
(2), (4) Date: Oct. 8, 2010

(87) PCT Pub. No.: WO2009/124974
PCT Pub. Date: Oct. 15, 2009

(65) Prior Publication Data
US 2011/0034326 A1 Feb. 10, 2011

(30) Foreign Application Priority Data
Apr. 9, 2008 (EP) .................... 08154240

(51) Int. Cl.
*B01J 23/00* (2006.01)
*B32B 5/16* (2006.01)
*B32B 9/00* (2006.01)
*B32B 15/02* (2006.01)
*B32B 17/02* (2006.01)
*B32B 19/00* (2006.01)
*B32B 21/02* (2006.01)
*B32B 23/02* (2006.01)
*B32B 27/02* (2006.01)

(52) U.S. Cl.
USPC ........... 502/305; 502/315; 502/319; 502/321; 502/527.12; 502/527.15; 428/403

(58) Field of Classification Search
USPC ................. 502/305, 315, 319, 321, 527.12, 502/527.15; 428/403
See application file for complete search history.

(56) References Cited

U.S. PATENT DOCUMENTS

| | | | |
|---|---|---|---|
| 3,799,886 A | 3/1974 | Felice et al. | |
| 3,956,377 A * | 5/1976 | Dolhyj et al. | 562/535 |
| 4,259,211 A * | 3/1981 | Krabetz et al. | 502/178 |
| 4,297,247 A | 10/1981 | Krabetz et al. | |
| 4,305,843 A | 12/1981 | Krabetz et al. | |
| 5,637,546 A | 6/1997 | Tenten et al. | |
| 5,677,261 A | 10/1997 | Tenten et al. | |
| 5,910,608 A * | 6/1999 | Tenten et al. | 562/532 |
| 6,169,214 B1 * | 1/2001 | Tenten et al. | 568/476 |
| 7,022,877 B2 | 4/2006 | Dieterle et al. | |
| 7,482,500 B2 | 1/2009 | Johann et al. | |
| 7,518,016 B2 | 4/2009 | Dieterle et al. | |
| 7,524,792 B2 | 4/2009 | Dieterle et al. | |
| 7,589,046 B2 | 9/2009 | Dieterle et al. | |
| 7,667,073 B2 | 2/2010 | Dieterle et al. | |
| 2003/0007904 A1 * | 1/2003 | Tonkovich et al. | 422/180 |
| 2003/0187305 A1 | 10/2003 | Petzoldt et al. | |
| 2006/0201573 A1 | 9/2006 | Petzoldt et al. | |
| 2006/0205978 A1 | 9/2006 | Yunoki et al. | |
| 2008/0187467 A1 | 8/2008 | Dieterle et al. | |
| 2008/0214863 A1 | 9/2008 | Cremer et al. | |

FOREIGN PATENT DOCUMENTS

| | | |
|---|---|---|
| DE | 1642921 A1 | 5/1971 |
| DE | 2106796 A1 | 8/1972 |
| DE | 2626887 A1 | 12/1977 |
| DE | 2909670 A1 | 10/1980 |
| DE | 2909671 A1 | 10/1980 |
| DE | 102004025445 A1 | 2/2005 |
| DE | 10350822 A1 | 6/2005 |
| DE | 102005010645 A1 | 8/2005 |
| DE | 102007010422 A1 | 9/2008 |
| EP | 614872 A1 | 9/1994 |
| EP | 0630879 A1 | 12/1994 |
| EP | 0714700 A2 | 6/1996 |
| EP | 990636 A1 | 4/2000 |
| EP | 1106598 A2 | 6/2001 |
| EP | 1579910 A2 | 9/2005 |
| GB | 1203321 A | 8/1970 |
| WO | WO-95/11081 A1 | 4/1995 |
| WO | WO-02/49757 A2 | 6/2002 |
| WO | WO-2004/108267 A1 | 12/2004 |
| WO | WO-2004/108284 A1 | 12/2004 |
| WO | WO-2005/063658 A1 | 7/2005 |
| WO | WO-2008/104577 A1 | 9/2008 |

OTHER PUBLICATIONS

U.S. Appl. No. 12/937,219, filed Oct. 8, 2010, Czaja et al.

* cited by examiner

*Primary Examiner* — Patricia L Hailey
(74) *Attorney, Agent, or Firm* — Novak Druce Connolly Bove + Quigg LLP

(57) ABSTRACT

Coated catalysts comprising a catalytically active multimetal oxide comprising molybdenum. The coated catalyst comprises a support body, a first layer and a second layer. The first layer comprises a molybdenum oxide or a precursor compound which forms molybdenum oxide. The second layer comprises a multimetal oxide comprising molybdenum and at least one further metal.

4 Claims, No Drawings

COATED CATALYSTS COMPRISING A MULTIMETAL OXIDE COMPRISING MOLYBDENUM

CROSS-REFERENCE TO RELATED APPLICATIONS

This application is a national stage application (under 35 U.S.C. §371) of PCT/EP2009/054238, filed Apr. 8, 2009, which claims benefit of European application 08154240.9, filed Apr. 9, 2008, the contents of each of which are incorporated herein by reference in their entireties.

FIELD OF THE INVENTION

The present invention relates to coated catalysts comprising a catalytically active multimetal oxide comprising molybdenum.

BACKGROUND OF THE INVENTION

Processes for preparing coated catalysts of the aforementioned type are known, for example from WO 95/11081, WO 2004/108267, WO 2004/108284, US-A 2006/0205978, EP-A 714700 and DE-A 102005010645. The active composition is a multimetal oxide comprising molybdenum. The term "multimetal oxide" expresses the fact that the active composition, as well as molybdenum and oxygen, also comprises at least one further chemical element.

Catalysts of the aforementioned type are suitable, for example, for the catalysis of the heterogeneously catalyzed partial gas phase oxidation of acrolein to acrylic acid.

DE-A 10350822 and DE-A 102004025445 disclose that the heterogeneously catalyzed gas phase partial oxidation of acrolein to acrylic acid over one and the same fixed catalyst bed can be operated essentially continuously over prolonged periods. However, the activity of the fixed catalyst bed worsens in the course of operation.

In order nevertheless to be able to operate the fixed catalyst bed, whose exchange is comparatively inconvenient and costly, for as long as possible, attempts are made in the prior art in a wide variety of ways to counteract the aging process of the fixed catalyst bed.

EP-A 990636 and EP-A 1106598 propose substantially compensating for the reduction in the activity of the fixed catalyst bed by, in the course of the operating time, under otherwise substantially constant operating conditions, gradually increasing the temperature of the fixed catalyst bed, in order to essentially maintain the acrolein conversion in single pass of the reaction gas mixture through the fixed catalyst bed. A disadvantage of this procedure is that, with increasing elevation of the temperature of the fixed catalyst bed, the aging process is increasingly accelerated. Finally, the catalyst bed has to be exchanged in its entirety.

DE-A 102004025445 proposes, for the long-term operation of the heterogeneously catalyzed partial gas phase oxidation of acrolein to acrylic acid, counteracting the deactivation of the fixed catalyst bed by increasingly elevating the working pressure in the gas phase with increasing operating time of the fixed catalyst bed. A disadvantage of this procedure is that, with increasing working pressure in the heterogeneously catalyzed partial gas phase oxidation, elevated compression outputs are required.

EP-A 614872 recommends prolonging the lifetime of the fixed catalyst bed by, after an operating time of the fixed catalyst bed of several years, interrupting the process for partial oxidation and, at elevated temperature, conducting a regeneration gas mixture composed of oxygen, steam and inert gas through the fixed catalyst bed, and then continuing the partial oxidation.

What is common to the above-described prior art processes for prolonging the lifetime of the fixed catalyst bed is that they do not preventatively counteract the deactivation of the fixed catalyst bed, but rather attempt to counteract the consequences of the deactivation which has already occurred.

EP-A 0 630 879 describes a process for catalytic oxidation of propene, isobutene or tert-butanol over a multimetal oxide catalyst comprising molybdenum, bismuth and iron, which works in the presence of a molybdenum oxide which is essentially catalytically inactive. The presence of the molybdenum oxide inhibits the deactivation of the multimetal oxide catalyst. The molybdenum oxide may be present in the form of separate molybdenum oxide particles, if appropriate on a support, in a mixture with particles of the multimetal oxide catalyst. Also mentioned is the possibility of preparing a mixture of pulverulent molybdenum oxide and pulverulent multimetal oxide catalyst, and of extruding the mixture to form shaped catalyst bodies or of applying it to a support.

German patent application DE 10 2007 010 422, which was yet to be published at the priority date of the present application, describes counteracting a deactivation of coated catalysts for the heterogeneously catalyzed partial gas phase oxidation of acrolein to acrylic acid, whose active composition is a finely divided multielement oxide which comprises Mo and V and has been applied to a support body, by adding to the catalytically active composition composed of the multimetal oxide comprising Mo and V an oxide of molybdenum or a compound of molybdenum from which an oxide of molybdenum forms. The coated catalyst is coated with a mixture of molybdenum oxide or of the precursor compound and the multimetal oxide.

BRIEF SUMMARY OF THE INVENTION

It is an object of the invention to provide catalysts based on molybdenum-comprising multimetal oxides, which have improved deactivation behavior.

The object is achieved by a coated catalyst comprising
(a) a support body,
(b) a first layer comprising molybdenum oxide or a precursor compound which forms molybdenum oxide,
(c) a second layer comprising a catalytically active multimetal oxide comprising molybdenum and at least one further metal.

This object is further achieved by a process for preparing the inventive coated catalysts, in which a first layer composed of a molybdenum oxide or of a precursor compound which forms molybdenum oxide is applied to a support body by means of a binder, the support body coated with the first layer is, if appropriate, dried and calcined, and a second layer of a molybdenum-comprising multimetal oxide is applied to the first layer by means of a binder, and the support body coated with the first and second layer is dried and calcined.

The object is further achieved by the use of the inventive coated catalysts in processes for catalytic gas phase oxidation of organic compounds.

DETAILED DESCRIPTION OF THE PREFERRED EMBODIMENTS

The first layer may comprise a molybdenum oxide or a precursor compound which forms molybdenum oxide. The precursor compound is a compound of molybdenum from which, under the action of elevated temperature and in the presence of molecular oxygen, an oxide of molybdenum forms. The action of the elevated temperature and of the molecular oxygen can proceed after the application of the precursor compound to the surface of the support body. For this purpose, a thermal treatment can be effected, for example under an oxygen or air atmosphere.

Examples of suitable precursor compounds other than an oxide of molybdenum include ammonium molybdate [$(NH_4)_2MoO_4$] and ammonium polymolybdates such as ammonium heptamolybdate tetrahydrate [$(NH_4)_6Mo_7O_{24} \cdot 4 H_2O$]. A further example is molybdenum oxide hydrate ($MoO_3 \cdot xH_2O$). However, molybdenum hydroxides are also useful as such precursor compounds.

The precursor compound can also be converted to an oxide of molybdenum by the action of heat and oxygen actually during the use of the catalyst in the catalytic gas phase oxidation.

However, the first layer preferably comprises an oxide of molybdenum. This is understood to mean a substance which consists only of Mo and O to an extent of $\geq 98\%$ by weight, preferably to an extent of $\geq 99\%$ by weight and more preferably to an extent of $\geq 99.9\%$ by weight and more. A particularly preferred molybdenum oxide is molybdenum trioxide ($MoO_3$).

Further suitable molybdenum oxides are, for example, $Mo_{18}O_{52}$, $Mo_8O_{23}$ and $Mo_4O_{11}$ (cf., for example, Surface Science 292 (1993) 261-6, or J. Solid State Chem. 124 (1996) 104).

In general, the specific surface area $S_M$ of a suitable molybdenum oxide is $\leq 10$ m$^2$/g, preferably $\leq 5$ m$^2$/g and more preferably $\leq 2$ m$^2$/g. In general, the specific surface area $S_M$ will, however, be $\geq 0.01$ m$^2$/g, frequently $\geq 0.05$ m$^2$/g and in many cases a 0.1 m$^2$/g. The specific surface area is understood to mean the BET surface area (determined by gas adsorption ($N_2$) according to Brunauer-Emmet-Teller (BET)). The above statements regarding $S_M$ apply especially when the finely divided molybdenum oxide is $MoO_3$. The reason for the advantage of a low value for $S_M$ is that molybdenum oxide with a low value for $S_M$ behaves substantially inertly in the context of an oxidative alkane dehydrogenation.

Particle diameter distributions and particle diameters $d_x$ discerned therefrom (e.g. $d_{10}$, or $d_{50}$, or $d_{90}$) are based on determinations to ISO 13320 with the Malvern Mastersizer S laser diffraction spectrometer (Malvern Instruments, Worcestershire WR 14 1AT, United Kingdom). The particle diameters $d_x$ reported as the test result are defined such that X% of the total particle volume consists of particles having this diameter or a smaller diameter.

To prepare the inventive catalysts, in general, precursor compounds or molybdenum oxides, especially $MoO_3$, for which 0.1 µm $\leq d_{50} \leq 800$ µm, preferably 0.5 µm $\leq d_{50} \leq 600$ µm, more preferably 0.75 µm $\leq d_{50} \leq 400$ µm and most preferably 1 µm $\leq d_{50} \leq 200$ µm, are used. In principle, the granularity of the precursor compound or of the molybdenum oxide (e.g. $MoO_3$) is adjusted to the desired thickness $T_A$ of the first layer on the surface of the support body. In general, $d_{50}$ will be $\leq T_A$, preferably $\leq 0.75 \cdot T_A$, more preferably $\leq 0.5 \cdot T_A$ and most preferably $\leq 0.3 \cdot T_A$. Normally, $d_{50}$ will, however, be $\geq 0.001 \cdot T_A$, or $\geq 0.01 \cdot T_A$, frequently $\geq 0.05 \cdot T_A$ and in many cases $\geq 0.1 \cdot T_A$.

In principle, a suitable molybdenum oxide (e.g. $MoO_3$) may be obtained from another Mo-comprising precursor compound. For this purpose, the starting material may, for example, be ammonium heptamolybdate tetrahydrate [$(NH_4)_6Mo_7O_{24} \cdot 4 H_2O$]. For example, thermal treatment at 350° C. for 3 hours in an air stream likewise having a temperature of 350° C. converts it to $MoO_3$. The granularity of the $MoO_3$ can be adjusted as required in any desired manner by appropriate grinding and screening. It is also possible in a corresponding manner to adjust the specific surface area of the $MoO_3$ as desired. With increasing duration of the thermal treatment and/or elevation of the temperature of the thermal treatment (on completion of $MoO_3$ formation under inert gas or under a gas atmosphere comprising molecular oxygen, for example air), the specific surface area decreases.

On completion of formation of the $MoO_3$ at 350° C., a thermal treatment at from 550 to 650° C. in an air stream having a corresponding temperature for from 4 to 8 hours is generally sufficient to reduce the specific surface area $S_M$ of the $MoO_3$ to a value of $\leq 2$ m$^2$/g.

However, it is also possible to use commercially available molybdenum oxides. A suitable example for the process according to the invention is $MoO_3$ from the Climax Molybdenum Marketing Corporation (Phoenix, USA), which has an Mo content of 66.60% by weight and a specific surface area $S_M$ of 3.7 m$^2$/g (trade name: "pure Moly Oxide Crystalline POC").

In general, the aforementioned $MoO_3$ additionally has the following extraneous constituent specification: Na$\leq 8$ ppm by weight, K$\leq 29$ ppm by weight, Fe$\leq 4$ ppm by weight, Pb$\leq 1$ ppm by weight, Al$\leq 4$ ppm by weight, Cr$\leq 2$ ppm by weight, Ca$\leq 2$ ppm by weight, Cu$\leq 2$ ppm by weight, Mg$\leq 5$ ppm by weight, Ni$\leq 2$ ppm by weight, Si$\leq 5$ ppm by weight, Sn$\leq 1$ ppm by weight, and Ti$\leq 2$ ppm by weight.

However, it is also possible in accordance with the invention to use $MoO_3$ from the Climax Molybdenum Marketing Corporation of the "POS" commercial type. Alternatively, the commercial $MoO_3$ used for the process according to the invention may also be $MoO_3$ from H. C. Starck, D-38615 Goslar (trade name: "Molybdenum Trioxide I"). This has a specific surface area $S_M$ of 1 m$^2$/g. The Mo content of this $MoO_3$ is 66.6% by weight. This has the following extraneous component specification: NH$_4 \leq 0.01\%$ by weight, Al$\leq 10$ ppm by weight, Ca$\leq 5$ ppm by weight, Co$\leq 10$ ppm by weight, Cr$\leq 5$ ppm by weight, Cu$\leq 5$ ppm by weight, Fe$\leq 10$ ppm by weight, K$\leq 80$ ppm by weight, Mg$\leq 5$ ppm by weight, Mn$\leq 10$ ppm by weight, Na$\leq 20$ ppm by weight, Ni$\leq 5$ ppm by weight, P$\leq 10$ ppm by weight, Pb$\leq 10$ ppm by weight, Si$\leq 10$ ppm by weight, Sn$\leq 10$ ppm by weight, Ti$\leq 5$ ppm by weight, V$\leq 10$ ppm by weight, Zn$\leq 10$ ppm by weight, and Zr$\leq 10$ ppm by weight.

However, it is also possible to use "Molybdenum Trioxide" of the "II" types from H. C. Starck. Otherwise, it is also possible to use $MoO_3$ from the following manufacturers:

Metal-Tech.-Ltd. (Israel), purity>98% by weight, $S_M$=1.1 m$^2$/g;

Gulf Chemical (Texas, USA), 65.76% by weight Mo, $S_M$=1.2 m$^2$/g;

Nanjing Chemical Industries (China), 66.6% by weight Mo, $S_M$=0.8 m$^2$/g;

Kankal Exports (India), purity a 99% by weight, $S_M$=1.7 m$^2$/g;

Taiyo Koko Co., Ltd. (Japan), purity a 99.7% by weight, $S_M$=1.6 m$^2$/g;

Anhui Chizhou Huangshanling Lead and Zinc Mine (China), purity$\geq 99.7\%$ by weight, 66.5% by weight Mo, $S_M$=0.3 m$^2$/g;

CCl Moly B.V. (Netherlands), purity>99.5% by weight, >66% by weight Mo, $S_M$=2.5 m$^2$/g.

The catalytically active, molybdenum-comprising multimetal oxide may, for example, be a multimetal oxide which comprises Mo and V and is of the general formula (I)

$$Mo_{12}V_aX^1_bX^2_cX^3_dX^4_eX^5_fX^6_gO_n \qquad (I)$$

in which the variables are each defined as follows:
X$^1$=W, Nb, Ta, Cr and/or Ce,
X$^2$=Cu, Ni, Co, Fe, Mn and/or Zn,
X$^3$=Sb and/or Bi,
X$^4$=one or more alkali metals (Li, Na, K, Rb, Cs) and/or H,
X$^5$=one or more alkaline earth metals (Mg, Ca, Sr, Ba),
X$^6$=Si, Al, Ti and/or Zr,
a=1 to 6,
b=0.2 to 4,
c=0 to 18, preferably 0.5 to 18,
d=0 to 40,
e=0 to 2,
f=0 to 4,
g=0 to 40 and
n=a number which is determined by the valency and frequency of the elements in I other than oxygen.

Such multimetal oxides comprising molybdenum and vanadium are known as catalysts for the selective gas phase oxidation of propene to acrolein.

The catalytically active molybdenum-comprising multimetal oxide is preferably a multimetal oxide of the general formula II $$Mo_{12}Bi_aCr_bX^1_cFe_dX^2_eX^3_fO_y \qquad (II)$$

where
X$^1$=Co and/or Ni,
X$^2$=Si and/or Al,
X$^3$=Li, Na, K, Cs and/or Rb,
$0.2 \leq a \leq 1$,
$0 \leq b \leq 2$
$2 \leq c \leq 10$,
$0.5 \leq d \leq 10$,
$0 \leq e \leq 10$,
$0 \leq f \leq 0.5$ and
y=a number which, with the prerequisite of charge neutrality, is determined by the valency and frequency of the elements in II other than oxygen.

Preference is given to those coated catalysts whose catalytically active oxide composition, as X$^1$, comprises only Co. Preferred X$^2$ is Si, and X$^3$ is preferably K, Na and/or Cs; more preferably, X$^3$=K.

The stoichiometric coefficient a is preferably $0.4 \leq a \leq 1$, more preferably $0.4 \leq a \leq 0.95$. The stoichiometric coefficient b is preferably in the range of $0.1 \leq b \leq 2$ and more preferably in the range of $0.1 \leq b \leq 1$. The stoichiometric coefficient c is preferably in the range of $4 \leq c \leq 8$ and more preferably in the range of $6 \leq c \leq 8$. The value for the variable d is advantageously in the range of $1 \leq d \leq 5$ and particularly advantageously in the range of $2 \leq d \leq 4$. The stoichiometric coefficient f is appropriately $\geq 0$. Preferably, $0.01 \leq f \leq 0.5$ and, more preferably, $0.05 \leq f \leq 0.2$.

The value for the stoichiometric coefficient of oxygen y arises from the valency and frequency of the cations with the prerequisite of charge neutrality. Favorable inventive coated catalysts are those with catalytically active oxide compositions whose molar ratio of Co/Ni is at least 2:1, preferably at least 3:1 and more preferably at least 4:1. At best, only Co is present.

Such molybdenum-comprising multimetal oxides are suitable not only for the selective gas phase oxidation of propene to acrolein but also for the partial gas phase oxidation of other alkenes, alkanes, alkanones or alkanols to alpha,beta-unsaturated aldehydes and/or carboxylic acids. Examples include the preparation of methacrolein and methacrylic acid from isobutene, isobutane, tert-butanol or tert-butyl methyl ether.

Preferred gas phase oxidations for which the inventive coated catalysts are used are oxidative dehydrogenations of alkenes to 1,3-dienes, especially of 1-butene and/or 2-butene to 1,3-butadiene.

Finely divided Mo-comprising multimetal oxides for use in accordance with the invention are in principle obtainable by obtaining an intimate dry mixture from starting compounds of the elemental constituents of the catalytically active oxide composition and thermally treating the intimate dry mixture at a temperature of from 150 to 350° C.

To prepare suitable finely divided multimetal oxide compositions of this type and other types, the starting materials are known starting compounds of the elemental constituents of the desired multimetal oxide composition other than oxygen in the particular stoichiometric ratio, and these are used to obtain a very intimate, preferably finely divided, dry mixture which is then subjected to the thermal treatment. The sources may either already be oxides or be those compounds which are convertible to oxides by heating in the presence of oxygen. In addition to the oxides, the starting compounds are therefore, in particular, halides, nitrates, formates, oxalates, acetates, carbonates or hydroxides.

Suitable starting compounds of Mo are also its oxo compounds (molybdates) or the acids derived therefrom.

Suitable starting compounds of Bi, Fe and Co are especially their nitrates.

The intimate mixing of the starting compounds can in principle be effected in dry form or in the form of aqueous solutions or suspensions.

Preference is given to effecting the intimate mixing in the form of aqueous solutions or aqueous suspensions. Particularly intimate dry mixtures are obtained in the mixing process described when the starting compounds are exclusively sources and starting compounds present in dissolved form. The solvent used is preferably water. Subsequently, the aqueous composition (solution or suspension) is dried and the intimate dry mixture thus obtained is, if appropriate, immediately treated thermally. Preference is given to effecting the drying process by spray-drying (the exit temperatures are generally from 100 to 150° C.) and immediately after the completion of the aqueous solution or suspension.

When the powder obtained is frequently found to be too fine for immediate further processing, it is appropriately kneaded with addition of water. In many cases, in the course of kneading, an addition of a lower organic carboxylic acid (e.g. acetic acid) is found to be advantageous. Typical added amounts are from 5 to 10% by weight, based on powder composition used. The kneaded composition obtained is subsequently appropriately shaped to extrudates, which are thermally treated as already described and then ground to a fine powder.

Support materials suitable for coated catalysts obtainable in accordance with the invention are, for example, porous or preferably nonporous aluminum oxides, silicon dioxide, zirconium dioxide, silicon carbide or silicates such as magnesium silicate or aluminum silicate (e.g. C 220 steatite from CeramTec). The materials of the support bodies are chemically inert.

The support bodies may have a regular or irregular shape, preference being given to regular-shaped support bodies with distinct surface roughness, for example spheres, cylinders or hollow cylinders with a grit layer. Their longest dimension is generally from 1 to 10 mm.

The support materials may be porous or nonporous. The support material is preferably nonporous (total volume of the pores based on the volume of the support body preferably $\leq 1\%$ by volume). An increased surface roughness of the support body generally causes an increased adhesive strength of the applied coating composed of first and second layers.

The surface roughness $R_Z$ of the support body is preferably in the range from 30 to 100 µm, preferably from 50 to 70 µm (determined to DIN 4768 sheet 1 with a "Hommel Tester for DIN-ISO surface parameters" from Hommelwerke). Particular preference is given to rough-surface support bodies from CeramTec composed of C 220 steatite.

Particularly suitable in accordance with the invention is the use of essentially nonporous, rough-surface, spherical supports composed of steatite (for example C 220 steatite from CeramTec), whose diameter is from 1 to 8 mm, preferably from 2 to 6 mm, more preferably from 2 to 3 or from 4 to 5 mm. However, also suitable is the use of cylinders as support bodies, whose length is from 2 to 10 mm and whose external diameter is from 4 to 10 mm. In the case of rings as support bodies, the wall thickness is additionally typically from 1 to 4 mm. Annular support bodies for use with preference have a length of from 2 to 6 mm, an external diameter of from 4 to 8 mm and a wall thickness of from 1 to 2 mm. In particular, rings of geometry 7 mm×3 mm×4 mm (external diameter× length×internal diameter) are also suitable as support bodies.

The coating thickness $T_A$ of the first layer composed of molybdenum oxide or of the precursor compound applied to the support body is generally from 5 to 1000 µm.

Preference is given to from 10 to 500 µm, particular preference to from 20 to 250 µm and very particular preference to from 30 to 150 µm.

The coating thickness $T_B$ of the second layer composed of a molybdenum-comprising multimetal oxide composition applied to the first layer is generally from 5 to 1000 µm.

Preference is given to from 10 to 500 µm, particular preference to from 20 to 250 µm and very particular preference to from 30 to 150 µm.

The granularity (fineness) of the Mo-comprising finely divided multimetal oxide is adjusted to the desired coating thickness $T_B$ in the same manner as the granularity of the molybdenum oxide or of the precursor compound. All statements made with regard to the longest dimension $d_L$ of the molybdenum oxide or of the precursor compound therefore apply correspondingly to the longest dimension $d_L$ of the finely divided Mo-comprising multimetal oxide.

The mass ratio of the second layer composed of multimetal oxide to the first layer composed of molybdenum oxide in the finished, calcined catalyst is generally from 100:1 to 1:1, preferably from 50:1 to 5:1.

The finely divided compositions (molybdenum oxide or precursor compound or molybdenum-comprising multimetal oxide) can be applied to the surface of the support body in accordance with the processes described in the prior art, for example as described in US-A 2006/0205978 and EP-A 0 714 700.

In general, the finely divided compositions are applied to the surface of the support body or to the surface of the first layer with the aid of a liquid binder. Useful liquid binders include, for example, water, an organic solvent or a solution of an organic substance (for example of an organic solvent) in water or in an organic solvent.

Examples of organic binders include mono- or polyhydric organic alcohols, for example ethylene glycol, 1,4-butanediol, 1,6-hexanediol or glycerol, mono- or polybasic organic carboxylic acids such as propionic acid, oxalic acid, malonic acid, glutaric acid or maleic acid, amino alcohols such as ethanolamine or diethanolamine, and mono- or polyfunctional organic amides such as formamide. Suitable organic binder promoters soluble in water, in an organic liquid or in a mixture of water and an organic liquid are, for example, monosaccharides and oligosaccharides such as glucose, fructose, sucrose and lactose.

Particularly advantageously, the liquid binder used is a solution consisting of from 20 to 98% by weight of water and from 2 to 80% by weight of an organic compound. The organic proportion in the aforementioned liquid binders is preferably from 2 to 50% by weight and more preferably from 5 to 20% by weight.

Preference is generally given to those organic binders or binder fractions whose boiling point or sublimation temperature at standard pressure (1 atm) is $\geq 100°$ C., preferably $\geq 150°$ C. Most preferably, the boiling point or sublimation point of such organic binders or binder fractions at standard pressure is simultaneously below the highest calcination temperature employed in the course of preparation of the finely divided multimetal oxide comprising the element Mo. Typically, this highest calcination temperature is $\leq 600°$ C., frequently $\leq 500°$ C. or $\leq 400°$ C., in some cases even $\leq 300°$ C.

Particularly preferred liquid binders are solutions which consist of *from* 20 to 98% by weight of water and from 2 to 80% by weight of glycerol. The glycerol content in these aqueous solutions is preferably from 2 to 50% by weight and more preferably from 5 to 20% by weight.

The molybdenum oxide or the precursor compound and the Mo-comprising finely divided multimetal oxide can be applied in such a way that the finely divided substance is dispersed in the liquid binder and the resulting suspension is sprayed onto moving and, if appropriate, hot support bodies, as described in DE-A 1642921, DE-A 2106796 and DE-A 2626887.

After the spray application has ended, as described in DE-A 2909670, the moisture content of the resulting coated catalysts can be reduced by passing hot air over.

After the first layer of molybdenum oxide or of the precursor compound has been applied, the coated support body can be dried and calcined. Subsequently, in the same way, the second layer of Mo-comprising multimetal oxide is applied to the first layer, dried and calcined. However, it is also possible in the manner described above to apply the second layer directly to the first layer, without drying and calcining beforehand, and only to dry and calcine the support body coated with the first and second layer. Preference is given to drying the coated support body after application of the first layer.

However, the support bodies will preferably first be moistened with the liquid binder and then the finely divided composition (molybdenum oxide or precursor compound) will be applied to the surface of the binder-moistened support body by rolling the moistened support bodies in the finely divided composition. To achieve the desired layer thickness, the above-described process is preferably repeated several times, i.e. the base-coated support body is in turn moistened and then coated by contact with dry finely divided composition.

After the first layer of molybdenum oxide or of the precursor compound has been applied, the coated support body can be dried and calcined. Subsequently, in the same way, the second layer of multimetal oxide is applied, and the support body coated with first and second layer is dried and calcined.

In general, the coated support body is calcined at a temperature of from 150 to 600° C., preferably from 270 to 500° C. The calcination time is generally from 2 to 24 h, preferably from 5 to 20 h. The calcination is carried out in an oxygenous atmosphere, preferably air and/or lean air. In one embodiment of the invention, the calcination is effected according to a temperature program in which calcination is effected at temperatures between 150 and 350° C., preferably from 200 to 300° C., for a total of from 2 to 10 h, followed by calcination at temperatures between 350 and 550° C., preferably from 400 to 500° C. For a calcination of the first layer before application of the second layer, a calcination temperature of approx. 300° C. is sufficient, preference being given to calcining at at least 400° C. after application of the second layer.

The molybdenum oxide, the precursor compound which forms molybdenum oxide and the catalytically active, molybdenum-comprising multimetal oxide composition may each comprise a pore former. This may be present in the finely divided compositions or be added to the liquid binder. Suitable pore formers are, for example, malonic acid, melamine, nonylphenol ethoxylate, stearic acid, glucose, starch, fumaric acid and succinic acid. Preference is given to stearic acid, nonylphenol ethoxylate and melamine. Pore formers are generally present in the compositions applied to the support body in amounts of from 1 to 40% by weight, preferably from 1 to 20% by weight, these data being based on the sum of all components of the particular layer (molybdenum oxide or precursor compound, pore former, binder, or multimetal oxide, pore former, binder).

For a performance of the process according to the invention on the industrial scale, the employment of the process disclosed in DE-A 2909671 is advisable, but preferably using the binders recommended in EP-A 714700. In other words, the support bodies to be coated are charged into a preferably tilted (the tilt angle is generally from 30 to 90°, rotating vessel (e.g. rotary pan or coating tank). The rotating vessel conducts the especially spherical, cylindrical or hollow cylindrical support bodies under two metering devices arranged in succession at a particular distance. The first of the two metering devices is appropriately a nozzle through which the support bodies rolling in the rotating pan are sprayed with the liquid binder to be used and moistened in a controlled manner. The second metering device is disposed outside the atomization cone of the liquid binder sprayed in and serves to supply the finely divided composition, for example by means of a shaking channel. The support spheres moistened in a controlled manner take up the active composition powder supplied, which is compacted as a result of the rolling motion on the outer surface of the cylindrical or spherical support bodies to give a cohesive coating.

If required; the support body base-coated in this way, in the course of the subsequent rotation, again passes through the spray nozzle, and is moistened in a controlled manner, in order to be able to take up a further layer of finely divided composition in the course of continued motion, etc. Intermediate drying is generally not required. The liquid binder used in accordance with the invention can be removed partly or completely by final supply of heat, for example by the action of hot gases such as $N_2$ or air.

A particular advantage of the above-described embodiment of the process according to the invention consists in the fact that it is possible to prepare, in one procedure, coated catalysts with coatings consisting of two or more different compositions in layer form. Remarkably, the process according to the invention brings about both completely satisfactory adhesion of the successive layers to one another and of the base layer to the surface of the support body. This is also true in the case of annular support bodies.

The present invention also provides for the use of the inventive coated catalysts in processes for catalytic gas phase oxidation of organic compounds, for example of propene to acrolein, of acrolein to acrylic acid, of isobutene or tert-butanol to methacrolein or methacrylic acid, or in processes for oxidative dehydrogenation of olefins to dienes. Among the above-described uses, particular preference is given to the use of the coated catalysts in processes for oxidative dehydrogenation of olefins to dienes, especially of 1-butene and/or 2-butene to butadiene.

The invention is illustrated in detail by the examples which follow.

EXAMPLES

Example 1

Preparation of a Precursor Composition A of Stoichiometry $Mo_{12}Co_7Fe_3K_{0.08}Bi_{0.6}Cr_{0.5}$ Solution A:
A 10 l stainless steel vessel was initially charged with 3200 g of water. With stirring by means of an anchor stirrer, 4.9 g of a KOH solution (32% by weight of KOH) were added to the initially charged water. The solution was heated to 60° C. 1066 g of an ammonium heptamolybdate solution $((NH_4)_6Mo_7O_{24} *4 H_2O$, 54% by weight of Mo) were then added in portions over a period of 10 minutes. The resulting suspension was stirred for a further 10 minutes.

Solution B:
A 5 l stainless steel vessel was initially charged with 1663 g of a cobalt (II) nitrate solution (12.4% by weight of Co) and heated with stirring (anchor stirrer) to 60° C. 616 g of an iron (III) nitrate solution (13.6% by weight of Fe) were then added in portions over a period of 10 minutes while maintaining the temperature. The resulting solution was stirred for a further 10 min. 575 g of a bismuth nitrate solution (10.9% by weight of Bi) were then added while maintaining the temperature. After stirring for a further 10 minutes, 102 g of chromium(III) nitrate were added in solid form in portions and the resulting dark red solution was stirred for a further 10 min.

Precipitation:
While maintaining the 60° C., solution B was pumped into solution A by means of a peristaltic pump within 15 minutes. During the addition and thereafter, the mixture was stirred by means of an intensive mixer (Ultra-Turrax). After the addition had ended, the mixture was stirred for a further 5 min.

Spray Drying:
The resulting suspension was spray-dried in a spray tower from NIRO (spray head No. F0 A1, speed 25000 rpm) over a period of 1.5 h. The reservoir temperature was kept at 60° C. The gas input temperature of the spray tower was 300° C., the gas output temperature was 110° C. The resulting powder had a particle size ($d_{90}$) of less than 40 μm.

Calcination:
The resulting powder was calcined batchwise (500 g) in a covered porcelain dish in a forced-air oven (500 l (STP)/h) at 460° C.

After the calcination and cooling had ended, 296 g of light brown powder (precursor composition A) were obtained.

Comparative Example

Preparation of a Comparative Coated Catalyst VS1

49.5 g of precursor composition A were applied to 424 g of support bodies (steatite spheres of diameter 2-3 mm with grit layer). To this end, the support was initially charged in a coating drum (capacity 2 l, angle of inclination of the central drum axis relative to the horizontal=30°). The drum was set in rotation (25 rpm). An atomizer nozzle operated with compressed air was used to spray approx. 32 ml of liquid binder (10:1 glycerol:water mixture) onto the support over the course of approx. 30 min (spraying air 500 l (STP)/h). The nozzle was installed such that the spray cone wetted the support bodies conveyed within the drum in the upper half of the roll-off zone. The fine pulverulent precursor composition A was introduced into the drum by means of a powder screw, and the point of powder addition was within the roll-off zone, but below the spray cone. The powder addition was metered in in such a way as to give rise to homogeneous distribution of the powder on the surface. On completion of the coating, the resulting coated catalyst composed of precursor composition A and the support body was dried in a drying cabinet at 120° C. for 2 hours.

Thereafter, the coated catalyst was calcined in a forced-air oven from Heraeus, Germany (model K, 750/2 S, capacity 55 l) at 455° C.

Example 2

Preparation of an Inventive Two-Layer Coated Catalyst (1st Layer: MoO$_3$ with Nonylphenol Ethoxylate as Pore Former, 2nd Layer: Precursor Composition A with Melamine as Pore Former)

24.7 g of MoO$_3$ were applied according to the procedure in VS1 to 400 g of support bodies (steatite spheres of diameter 2-3 mm with grit layer). In a departure from the method described under VS1, the pore former (2.47 g of nonylphenol ethoxylate, BASF Lutensol AP6) had to be dissolved in the binder (15 ml in total) and was not mixed with the molybdenum oxide powder, since it was a liquid product. The resulting product was S2a.

In a second step, coated catalyst S2 was prepared: 49.5 g of precursor composition A were mixed with 4.95 g of melamine. The resulting powder was applied to 424 g of S2a according to the procedure in VS1. Amounts consumed and procedures were identical to VS1.

The resulting two-layer coated catalyst was S2.

Example 3

Preparation of an Inventive Two-Layer Coated Catalyst (1st Layer: MoO$_3$, 2nd Layer: Precursor Composition A with Melamine Pore Former)

24.71 g of MoO$_3$ were applied to 400 g of support bodies (steatite spheres of diameter 2-3 mm with grit layer) according to the procedure in VS1. The amount of binder consumed was 10 ml; the application time was 15 min. In a departure from VS1, calcination was effected at 300° C. only for 120 min. The resulting product was S3a.

In a second step, coated catalyst S3 was prepared: 49.5 g of precursor composition A were intimately mixed with 4.95 g of melamine. The resulting powder was applied to 424 g of S3a according to the procedure in VS1. The amount of binder consumed was 31 ml; the application time was 43 min. The resulting two-layer coated catalyst was S3.

Example 4

Preparation of an Inventive Two-Layer Coated Catalyst (1st Layer: MoO$_3$, 2nd Layer: Precursor Composition A)

24.71 g of MoO$_3$ were applied to 400 g of support bodies (steatite spheres of diameter 2-3 mm with grit layer) according to the procedure in VS1. The amount of binder consumed was 13 ml; the application time was 24 min. In a departure from VS1, calcination was effected at 300° C. only for 120 min. The resulting product was S4a. In a second step, coated catalyst S4 was prepared as follows: 49.5 g of precursor composition A were applied to 425 g of S4a according to the procedure in VS1. The amount of binder consumed was 31 ml; the application time was 36 min. The resulting two-layer coated catalyst was S4.

The invention claimed is:
1. A coated catalyst comprising
   (a) a support body,
   (b) a first layer comprising a molybdenum oxide or a precursor compound which forms molybdenum oxide,
   (c) a second layer comprising a multimetal oxide comprising molybdenum and at least one further metal.
2. The coated catalyst according to claim 1, wherein the molybdenum oxide of the first layer is MoO$_3$.
3. The coated catalyst according to claim 1, wherein the molybdenum-comprising multimetal oxide of the second layer is a multimetal oxide of the general formula II

$$Mo_{12}Bi_aCr_bX^1_cFe_dX^2_eX^3_fO_y \qquad (II)$$

where
$X^1$=Co and/or Ni,
$X^2$=Si and/or Al,
$X^3$=Li, Na, K, Cs and/or Rb,
$0.2 \leq a \leq 1$,
$0 \leq b \leq 2$
$2 \leq c \leq 10$,
$0.5 \leq d \leq 10$,
$0 \leq e \leq 10$,
$0 \leq f \leq 0.5$ and
y=a number which, with the prerequisite of charge neutrality, is determined by the valency and frequency of the elements in II other than oxygen.
4. A process for preparing a coated catalyst according to claim 1, in which a first layer composed of the molybdenum oxide or the precursor compound which forms molybdenum oxide is applied to the support body by means of a binder, the support body coated with the first layer is, if appropriate, dried and calcined, and a second layer of the molybdenum-comprising multimetal oxide is applied to the resulting first layer by means of a binder, and the support body coated with the first and second layer is dried and calcined.

* * * * *